(12) United States Patent
Yonak et al.

(10) Patent No.: US 8,449,878 B2
(45) Date of Patent: *May 28, 2013

(54) PREBIOTIC FORMULATIONS FOR USE WITH PROBIOTICS TO INCREASE PROBIOTIC GROWTH RATE AND ACTIVITY

(75) Inventors: Sonja Lea Yonak, Prior Lake, MN (US); Randolph S. Porubcan, Victoria, MN (US)

(73) Assignee: Master Supplements, Inc., Victoria, MN (US)

( * ) Notice: Subject to any disclaimer, the term of this patent is extended or adjusted under 35 U.S.C. 154(b) by 246 days.

This patent is subject to a terminal disclaimer.

(21) Appl. No.: 13/118,613

(22) Filed: May 31, 2011

(65) Prior Publication Data

US 2012/0009239 A1    Jan. 12, 2012

Related U.S. Application Data

(60) Provisional application No. 61/363,172, filed on Jul. 9, 2010.

(51) Int. Cl.
*A01N 63/00* (2006.01)
*A01N 63/02* (2006.01)
*A61K 9/28* (2006.01)
*A61K 9/48* (2006.01)
*A61K 9/14* (2006.01)
*C12Q 1/02* (2006.01)
*C12P 7/56* (2006.01)
*C12N 1/20* (2006.01)
*C12N 1/04* (2006.01)

(52) U.S. Cl.
USPC ....... 424/93.45; 424/93.4; 424/400; 424/463; 424/474; 435/29; 435/139; 435/252.9

(58) Field of Classification Search
USPC ........ 424/93.4, 93.45, 400, 463, 474; 435/29, 435/139, 252.9
See application file for complete search history.

(56) References Cited

U.S. PATENT DOCUMENTS 3,897,307 A * 7/1975 Porubcan et al. ............... 426/61
4,518,696 A * 5/1985 Gehrman et al. .......... 435/252.9

OTHER PUBLICATIONS

BioGaia® Probiotic Drops. BioGaia AB Kungsbroplan 3$^{mt;epmubaubxmx}$, P.O. Box 3242, SE—10 364, Stockholm, Sweden Bulletin Published Oct. 2009. pp. 1-4, Market Launch 2004 (Italy and Sweden), 2007 in the U. S.A.*
Phillips' Colon Health Probiotics Blend Published at http://phillipsrelief.com/products/colon-health-probiotics-fiber, Printed Nov. 29, 2011.*
Permatrol from BioCare Published at http://www.health4youonline.com/health_supplements_biocare_b285-90.html. Printed Nov. 29, 2011.*
Natren http://www.probiotic-info.com/probiotic-supplements-compared/natren-probiotics.html. Printed Nov. 29, 2011.*

* cited by examiner

*Primary Examiner* — Jon P Weber
*Assistant Examiner* — Kailash C Srivastava
(74) *Attorney, Agent, or Firm* — Eric P. Mirabel (57) ABSTRACT

Naturally occurring lecithins and/or oleic acid stimulate the growth and lactic acid producing activity of *Lactobacillus* and *Bifidobacterium* species of probiotic bacteria, and replace polysorbate 80 for those products. They can be used in naturally occurring form, or where they are to be combined with probiotics in a carrier, or they can be treated to yield a stable powdered form of these naturally oily compounds. They can be sold as combined prebiotic/probiotic formulations in the same carrier, or sold as separate dietary supplements, e.g., in capsule or tablet form, to be used with the probiotic formulation as desired.

22 Claims, 8 Drawing Sheets

PREBIOTIC FORMULATIONS FOR USE WITH PROBIOTICS TO INCREASE PROBIOTIC GROWTH RATE AND ACTIVITY

RELATED APPLICATIONS

This application claims priority to U.S. Provisional No. 61/363,172, filed Jul. 9, 2010.

BACKGROUND

Prebiotics, which increase the in vivo growth rate or activity of probiotic bacteria like *Lactobacillus* and/or *Bifidobacterium*, are generally soluble fiber sources. Probiotics with or without prebiotics are fed to humans or animals to support intestinal health. Soluble fiber prebiotics are not digested by host animal digestive enzymes but rather, are the energy source for the probiotic species and are digested by enzymes produced by the probiotic species. Soluble fiber prebiotics enhance probiotic growth but are not required for growth.

There are some compounds that are semi-strict requirements for *Lactobacillus* and *Bifidobacterium* growth but that are not required for human or animal nutrition and which can serve as prebiotics. One such compound is polysorbate 80 that is contained in Lactobacilli MRS Broth (Difco Laboratories, Detroit, Mich.). When Lactobacilli or certain strains of Bifidobacteria are inoculated into this broth (containing 0.1% polysorbate 80) prolific growth results; whereas, in the absence of polysorbate 80, growth can be several logarithms lower. The inability of many individuals to experience the benefits of probiotic supplements may relate to the inability of probiotic strains to grow and colonize effectively in the absence of polysorbate 80.

The scientific literature reports that the oleic acid moieties in polysorbate 80 may provide its stimulating effect (See: Williams, W. L. et al, 1947, J. Biol. Chem., 170, 619-630). However, most probiotic strains are sensitive to the concentration of oleic acid in their growth media and respond negatively by producing less lactic acid (which is vital to obtaining strong probiotic benefits) when slight excesses of oleic acid are present. But these same strains do not respond negatively when excess polysorbate 80 is present. So it appears there is something unique to the polysorbate 80 stimulation effect, which oleic acid alone cannot duplicate.

The problems with using polysorbate 80 in commercial probiotic products when attempting to utilize its dramatic growth enhancing benefits are: 1) it is not a natural compound and is rejected by those consumers insisting on natural, organic ingredients; and 2) it reacts with and degrades freeze-dried probiotic strains when mixed directly with them. So, there is a need for an alternative natural prebiotic that can replace polysorbate 80 in commercial probiotic formulations, without the drawbacks mentioned above.

SUMMARY

Naturally occurring lecithins and/or oleic acid can stimulate the growth and lactic acid producing activity of *Lactobacillus* and *Bifidobacterium* species of probiotic bacteria, and replace polysorbate 80 as an additive for those products. They can be administered as either a stable powdered form of these naturally oily compounds (this process also reduces their chemical reactivity) or in their natural form.

This stable powder form of lecithins and/or oleic acid can be added directly to probiotic formulations containing sensitive, freeze-dried *Lactobacillus* and *Bifidobacterium* probiotic strains and enhance the growth (as measured by CFU (colony forming units)) and also enhance LAPA (lactic acid producing activity). These stable powders can also be separated from the probiotic formulations, and packaged and sold as separate dietary supplements, e.g., in capsule or tablet form, to be used with the probiotic formulation as desired—preferably in a form where they will be able to combine and assist the probiotic growth and activity once they reach the intestine. This is accomplished by incorporating them in a capsule or delivery mode that has an enteric coating.

Naturally occurring lecithins and/or oleic acid can also be administered separately from the probiotic formulation. Again, they should preferably be in a form where they will be able to combine and assist the probiotic growth and activity once they reach the intestine—e.g., by incorporating them in a capsule or delivery mode that has an enteric coating. For the stable powder form of the lecithins and/or oleic acid which are to be separately administered, they are first adsorbed to an adsorbent compound or composition, including calcium silicate, silicon dioxide, fumed silica, food grade clay substances such as kaolin and sodium bentonite, food starches such as Pure Dent B830 corn starch (Grain Processing Corp., Muscatine, Iowa), Perfectamyl D6 potato starch (National Starch-Avebe, Bridgewater, N.J.), and preferably to Hubersorb 600 (J.M. Huber Corp., Havre de Grace, Md.), a highly adsorbent form of calcium silicate. The formulation also preferably includes dry forms of microcrystalline cellulose and silica. The carrier is preferably 10-300% (by weight) of the adsorbent, and the silica is preferably 0.25 to 2% by weight of the final formulation, with the lecithin/oleic acid preferably at 5-40% of the final formulation weight.

For a formulation of the naturally occurring lecithins and/or oleic acid, the ratio of lecithin to oleic acid can preferably be from 95:5 by weight to 60:40, with a ratio of 90:10 more preferred. The lecithin can be any form of lecithin, preferably sunflower lecithin or soy lecithin, and more preferably sunflower lecithin. The preferred embodiment is 90:10, sunflower lecithin: oleic acid, with an antioxidant, for example, natural Vitamin E (d-alpha tocopherol), at 0.01% to 5.0%, with 0.1% by weight preferred, of the final formulation.

The dry prebiotic formulation can be incorporated into a final product, including probiotics, at between 1 and 100% of the final product formulation, with 10-20% preferred. Such final product is preferably taken with a carbohydrate snack of about 50 g in weight, making the lecithin/oleic acid at about 0.01%-5.0% of the total weight of the products ingested, with 0.1% by weight being preferred.

BRIEF DESCRIPTION OF THE DRAWINGS

FIG. 1A shows the enhanced growth.

FIG. 2A shows the enhanced growth.

FIG. 3A shows the enhanced growth.

FIG. 4A shows the enhanced growth.

FIG. 5A shows the enhanced growth.

FIG. 6A shows the enhanced growth.

FIG. 7A shows the enhanced growth.

FIG. 8A shows the enhanced growth.

DETAILED DESCRIPTION

Probiotic formulations are useful in treating a number of conditions, including irritable bowel syndrome, Crohn's disease, remission of ulcerative colitis and preventing relapse of Crohn's disease and the recurrence of pouchitis (following surgery), colitis, ileitis, diverticulitis, re-establishing the intestinal tract's beneficial microflora that are destroyed by the antibiotics used to treat diarrhea (including traveler's diarrhea), vaginal yeast infections, constipation, heartburn, bloating, indigestion, flatulence and poor nutrient absorption. Conditions leading to indigestion and lack of nutrient absorption by the intestine are also treated by probiotics. The average person carries about 4-5 pounds of fecal matter in their intestine, and adding probiotics helps to reduce the volume. With the prebiotic formulation herein, the volume of fecal expelled per unit time is generally increased, thereby reducing the carried fecal matter.

As prebiotics enhance the efficacy of probiotics, they should be used with them when feasible. Probiotics dosing should be at least about 30-40 billion CFUs every three days, to as much as 180 billion per day, depending on severity of disease or condition and patient response. There is no known toxic level or excessive dosage. The prebiotics dose to effectively support each probiotic dosage is about 10 to 100 mg of the active ingredient(s)—lecithin and/or oleic acid—more preferably, about 20-50 mg of the active ingredients, for each probiotics dose. If more probiotic is taken, the prebiotic can be similarly increased for maximum effect.

The prebiotics of this invention can be in the same capsule or formulation as the probiotics, or in a separate dosage form. The prebiotics should be in a separate dosage form if they are naturally occurring, as opposed to adsorbed. The prebiotics of this invention may be taken with carbohydrate or fiber to increase their effectiveness. Prebiotic formulations are often probiotic strain dependent. Some *Lactobacillus* strains, for example, respond best to a form of lecithin derived from sunflowers (Sunflower Lecithin) while others show no preference to lecithin type and respond equally well to soy lecithin. Other strains show a synergistic response when lecithin is used together with oleic acid. Verification of the properties of the formulation was made by examining the growth (measured in NTU turbidity units) and lactic acid producing activity (measured by titration and pH) in MRS broth made up such that polysorbate 80 could either be retained (as control) or be removed and substituted by a preferred lecithin and oleic acid mixture, which is 90% sunflower lecithin and 10% oleic acid by weight, and includes 0.1% by weight Vitamin E.

Figure 1A:
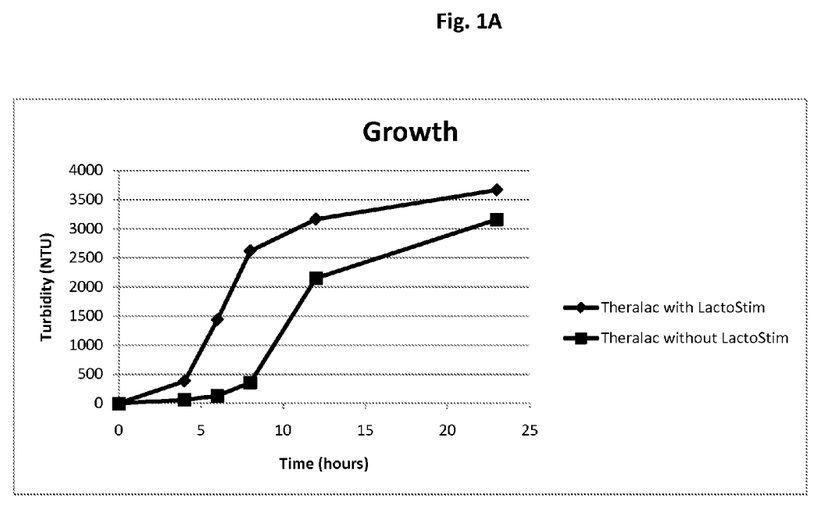
Figure 1B:
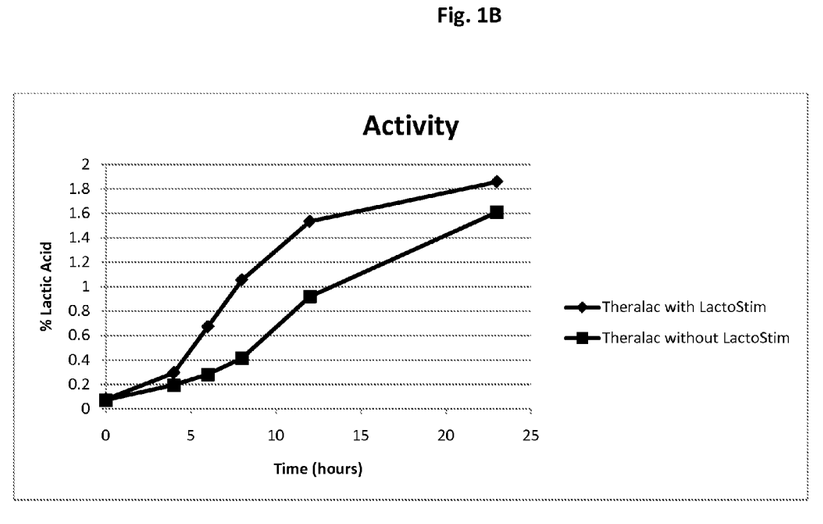
FIG. 1B shows the enhanced activity, with naturally-occurring sunflower lecithin and oleic acid at a 90:10 weight ratio, including Vitamin E and the probiotic bacterial species in the product Theralac®, (Master Supplements, Inc., (Victoria, Minn.)), which primarily consist of *Lactobacillus* and *Bifidobacterium* strains, with some initial dry-form Lactostim® (Master Supplements, Inc., (Victoria, Minn.)) present.
Figure 2A:
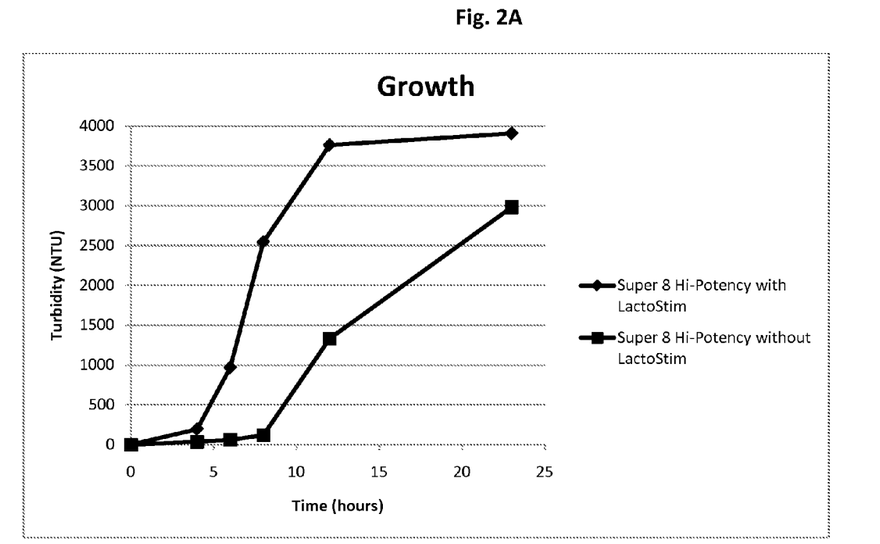
Figure 2B:
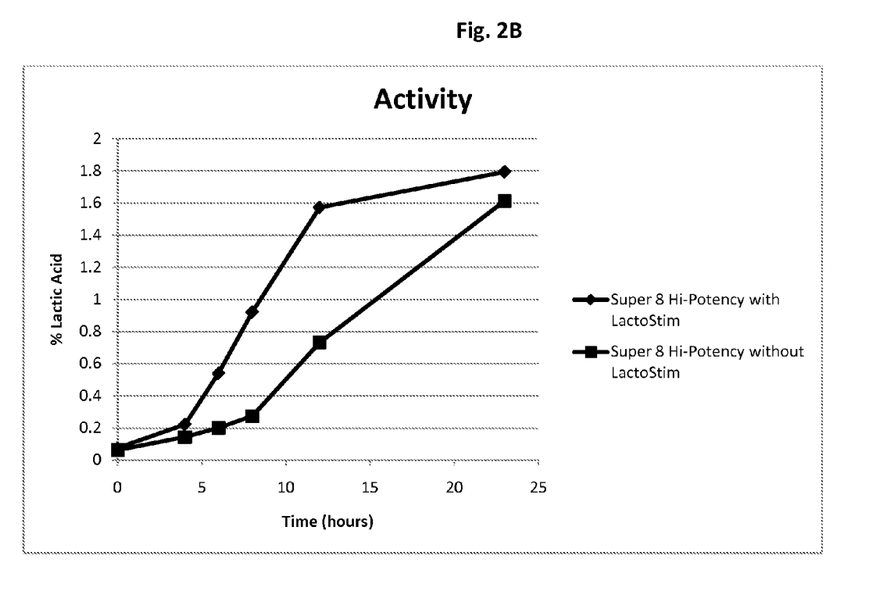
FIG. 2B shows the enhanced activity, with naturally-occurring sunflower lecithin and oleic acid at a 90:10 weight ratio, including Vitamin E and the probiotic bacterial species in Udo's Choice Super 8 Hi Potency™, which primarily consist of *Lactobacillus* and *Bifidobacterium* strains.
Figure 3A:
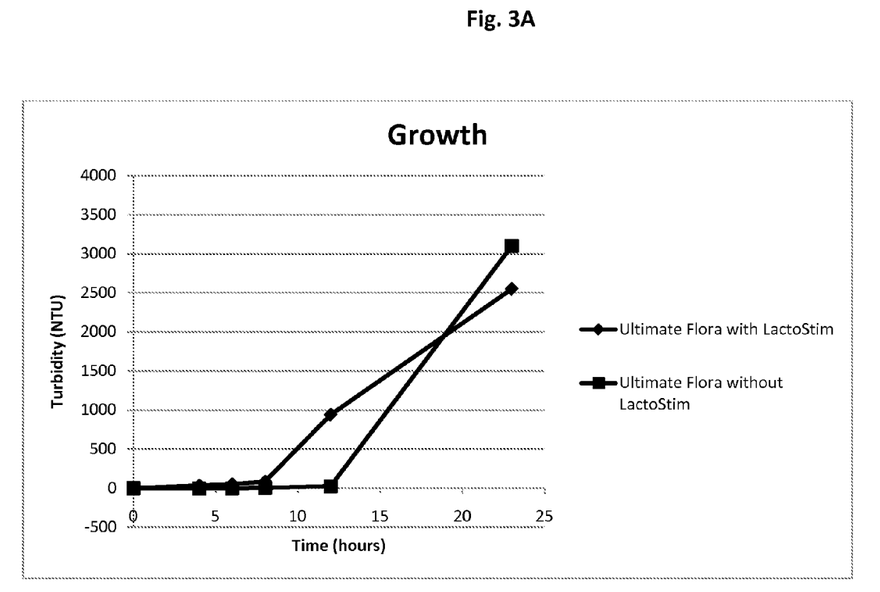
Figure 3B:
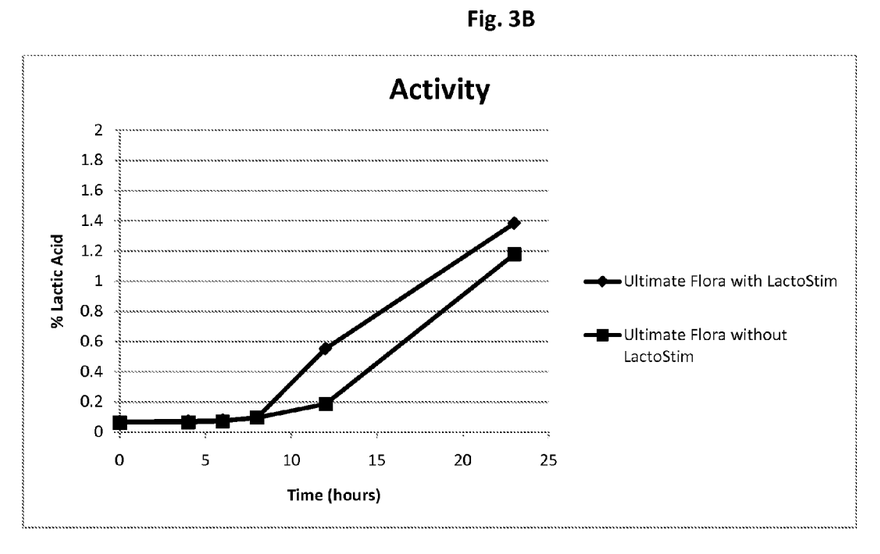
FIG. 3B shows the enhanced activity, with naturally-occurring sunflower lecithin and oleic acid at a 90:10 weight ratio, including Vitamin E and the probiotic bacterial species in Ultimate Flora™ from Renew Life, which consists of *Lactobacillus* and *Bifidobacterium* strains.
Figure 4A:
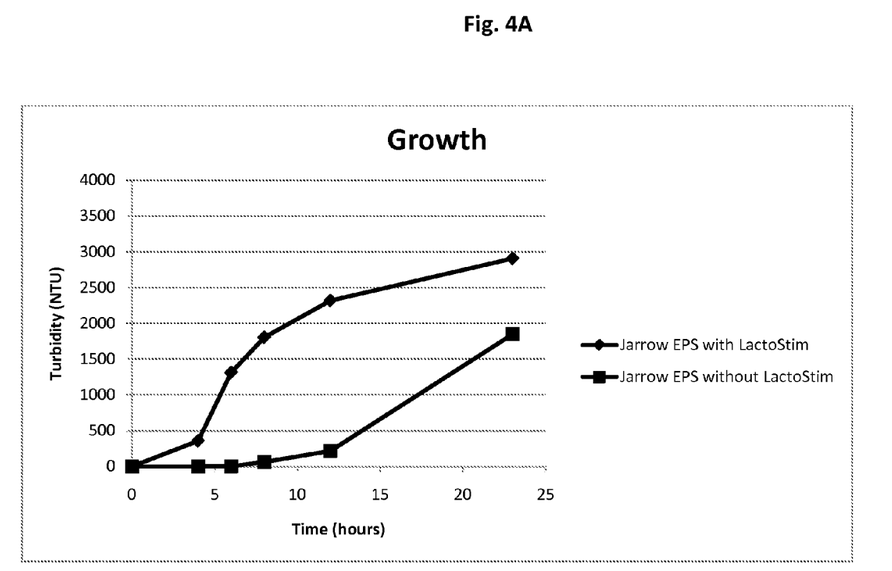
Figure 4B:
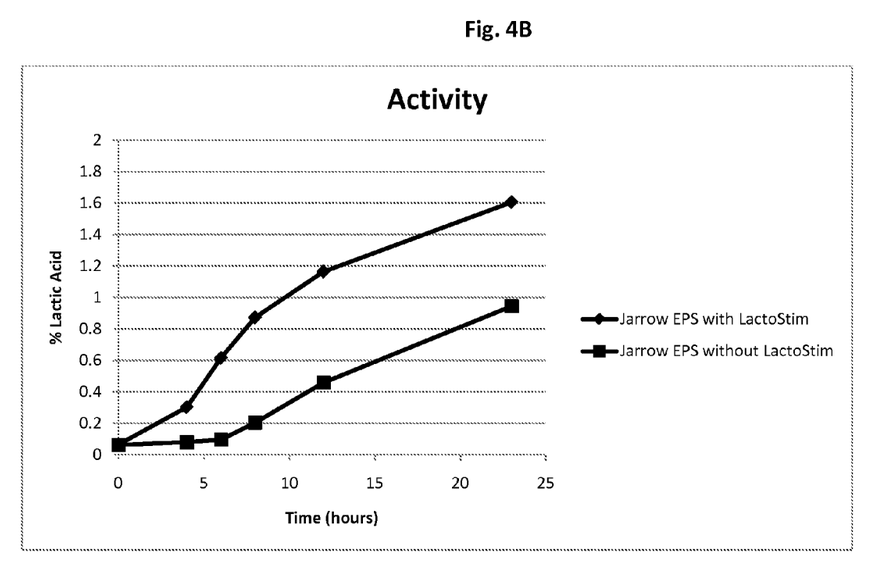
FIG. 4B shows the enhanced activity, with naturally-occurring sunflower lecithin and oleic acid at a 90:10 weight ratio, including Vitamin E and the probiotic bacterial species in Jarrow-Dolphius EPS by Jarrow Formulas, which primarily consist of *Lactobacillus* and *Bifidobacterium* strains.
Figure 5A:
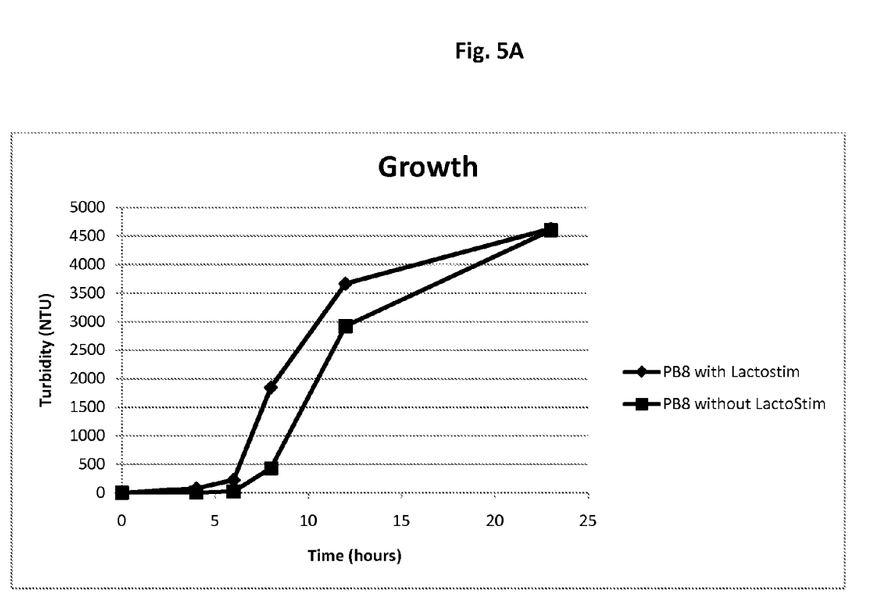
Figure 5B:
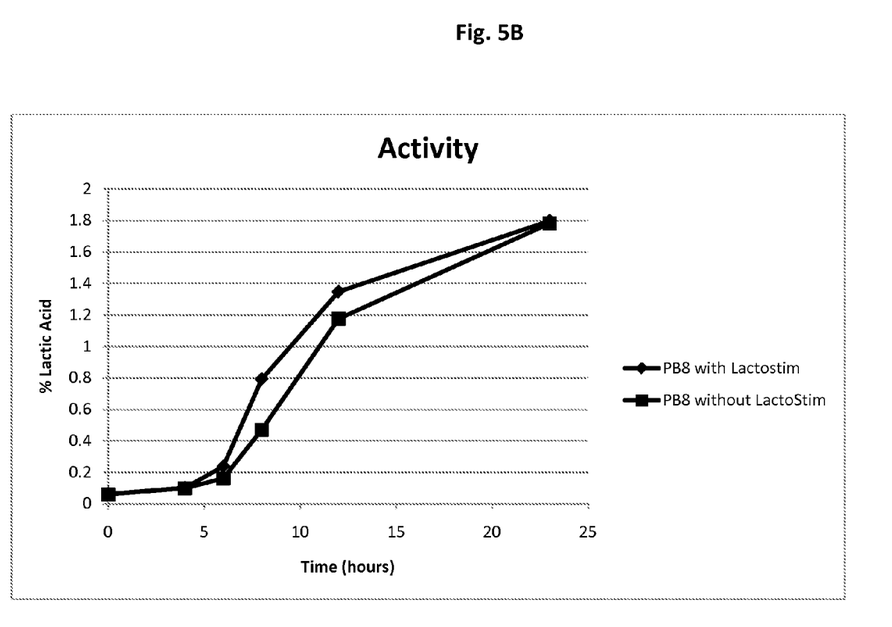
FIG. 5B shows the enhanced activity, with naturally-occurring sunflower lecithin and oleic acid at a 90:10 weight ratio, including Vitamin E and the probiotic bacterial species in PB8 by Nutrition Now, which primarily consist of *Lactobacillus* and *Bifidobacterium* strains.
Figure 6A:
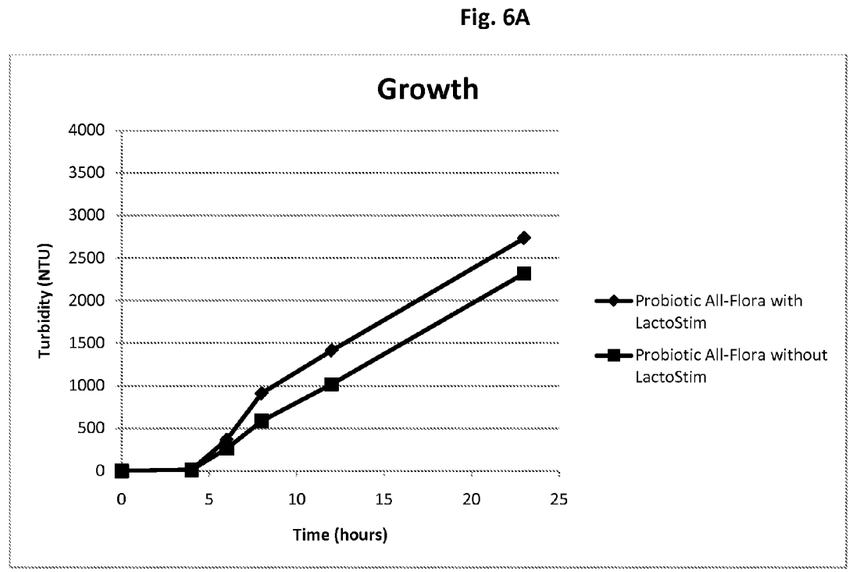
Figure 6B:
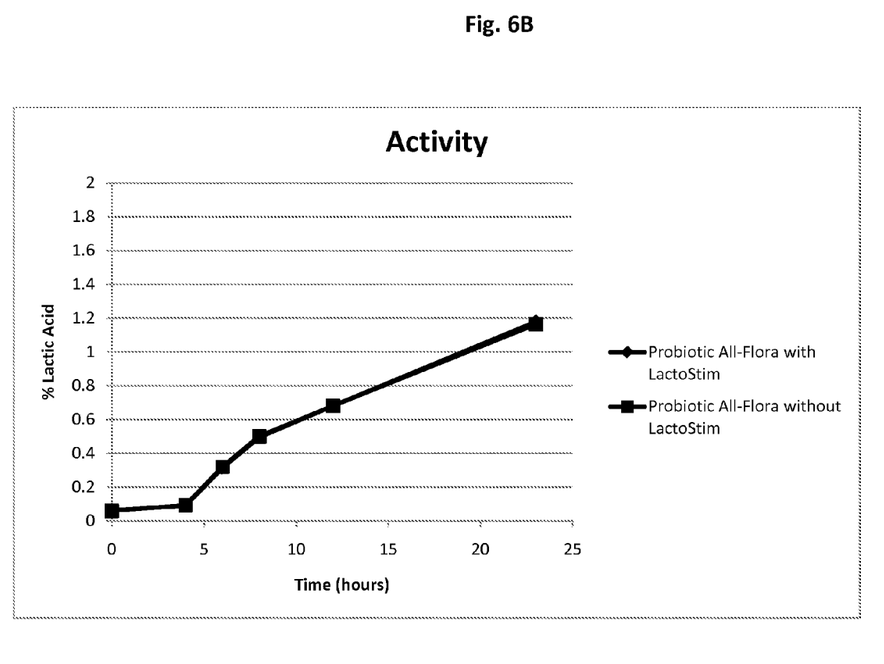
FIG. 6B shows the enhanced activity, with naturally-occurring sunflower lecithin and oleic acid at a 90:10 weight ratio, including Vitamin E and the probiotic bacterial species in All Flora by New Chapter, which primarily consist of *Lactobacillus* and *Bifidobacterium* strains.
Figure 7A:
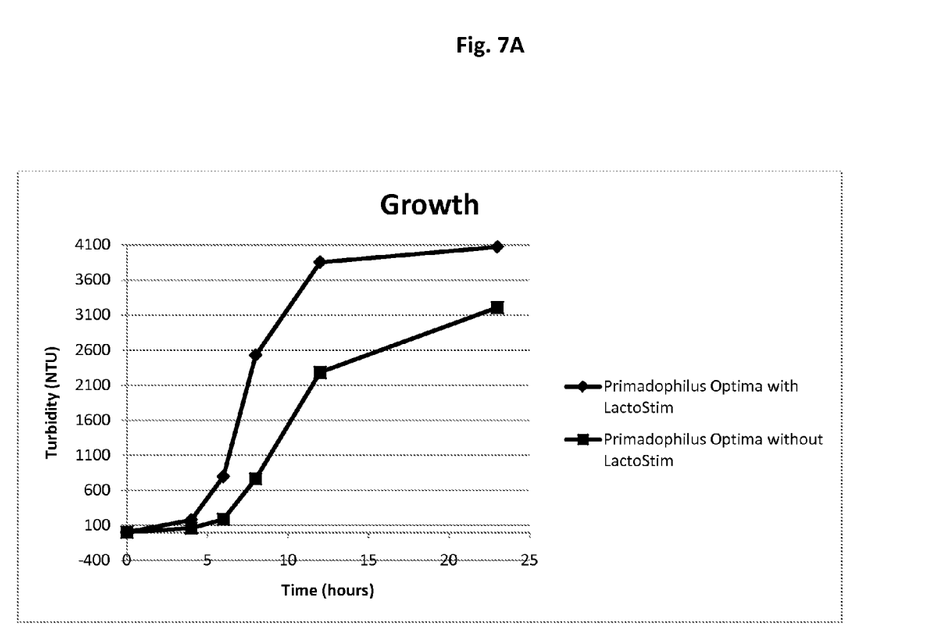
Figure 7B:
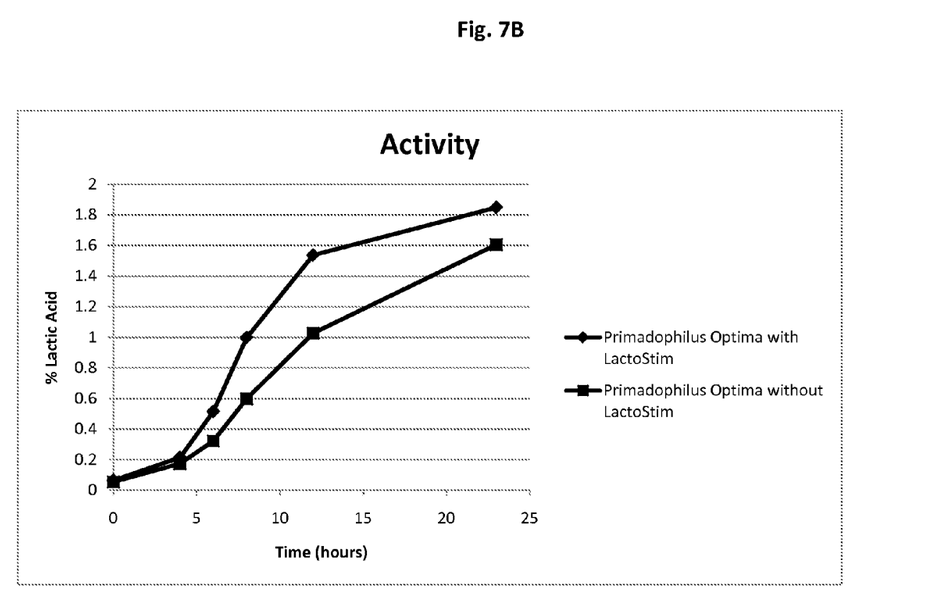
FIG. 7B shows the enhanced activity, with naturally-occurring sunflower lecithin and oleic acid at a 90:10 weight ratio, including Vitamin E and the probiotic bacterial species in Primadophilus Optima by Natures Way, which primarily consist of *Lactobacillus* and *Bifidobacterium* strains.
Figure 8A:
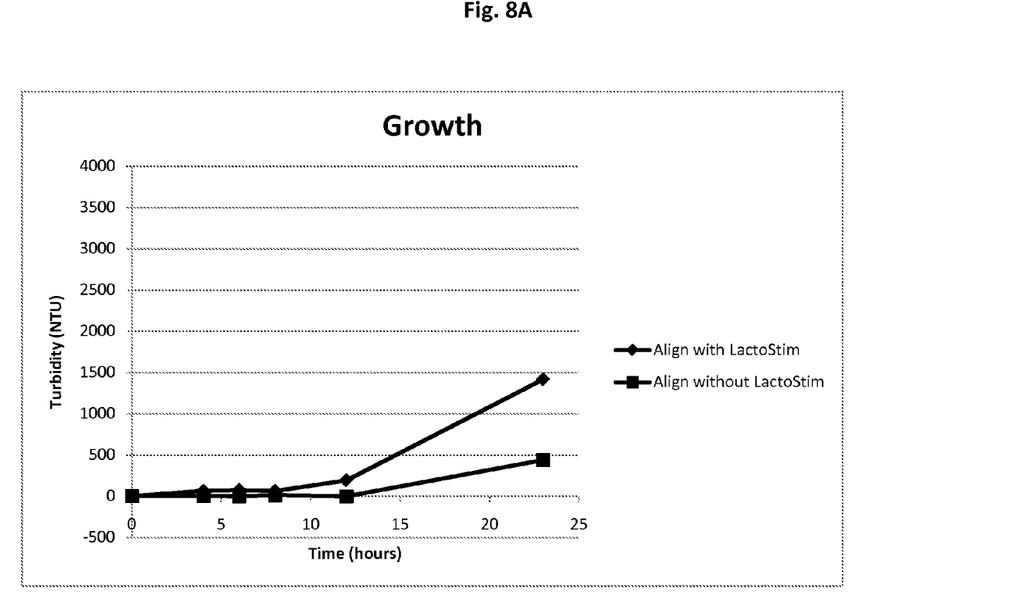
Figure 8B:
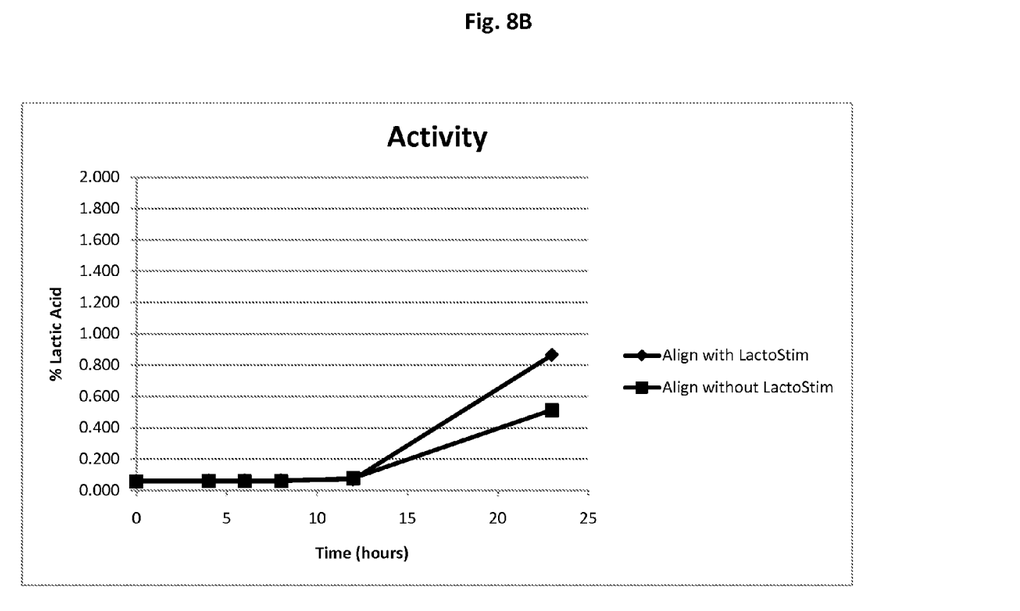
FIG. 8B shows the enhanced activity, with naturally-occurring sunflower lecithin and oleic acid at a 90:10 weight ratio, including Vitamin E and the *Bifidobacterium* strain in Align, by Proctor & Gamble.

The growth and activity results shown in FIGS. 1A to 8B were with the commercial probiotic products indicated in the figures, using the liquid form of sunflower lecithin and oleic acid (90:10 weight ratio and including 0.1% by weight Vitamin E) or not, as indicated. The growth media was the MRS media prepared as described in Example 3 below, and the testing of growth and activity was as described in Example 4 below.

Example 1

Preparing Prebiotic Formulations Including One or More of Sunflower Lecithin, Soy Lecithin and Oleic Acid The active ingredients in the formulation: sunflower lecithin, soy lecithin and oleic acid, are oily, non-aqueous liquids that should be rendered into stable, non-reactive powders to render them suitable for combination with probiotics in the same formulation by, for example, the following process.

Step 1: Combining Active Ingredients

The active ingredients (e.g., sunflower lecithin, soy lecithin and/or oleic acid) are mixed into an adsorbent material under non-aqueous conditions. The adsorbent is selected from a large class of substances including but not limited to: calcium silicate, silicon dioxide, fumed silica, food grade clay substances such as kaolin and sodium bentonite, food starches such as Pure Dent B830 corn starch (Grain Processing Corp., Muscatine, Iowa) and Perfectamyl D6 potato starch (National Starch-Avebe, Bridgewater, N.J.). One preferred substance is Hubersorb 600 (J.M. Huber Corp., Havre de Grace, Md.), a highly adsorbent form of calcium silicate.

The adsorbent is first placed in a suitable mixer such as a Hobart fitted with either a wire wisp or a pizza dough mixing blade and, with the mixer running at medium speed (40-60 RPM). The active ingredient is added slowly by pouring or pumping onto the adsorbent. It is important to modulate the rate of addition such that the adsorbent is not overloaded to where lumps form.

The active ingredient(s) should be homogeneously premixed with any other necessary or desired ingredients (for example, Vitamin E; including any of the D, L or a mix of the D and L isomers) prior to adding to the adsorbent if such a mixture is required. The Vitamin E is preferably 0.05 to 2% of the active ingredients, by weight. The active ingredients are preferably mixed with Vitamin E separately, and this mixture is then added to the adsorbent in the Hobart under constant agitation. For other proportions, if Hubersorb 600 is selected as the adsorbent for the vitamin E treated sunflower lecithin, active ingredient can be up to about 150% of the weight of the Hubersorb 600. If Perfectamyl D6 potato starch is used instead as the adsorbent, then active ingredient added may be only about 12% of its weight. A trial an error process is required when trying new adsorbent materials from the groups listed. Once all active ingredient(s) have been added, one proceeds to Step 2.

Step 2: Adding Additional Carrier

Once all the active ingredient(s) have been adsorbed, a second carrier ingredient selected from a different class is added to the mixture in the Hobart. This ingredient attenuates the mixture rendering it into smaller particles. The preferred class of ingredients here are the driest forms of microcrystalline cellulose available; i.e., pharmaceutical grades such as Microcel MC-132 (Blanver, Boca Raton, Fla.) or the Avicell PH112 brand (FMC Corporation, Philadelphia, Pa.). The amount added will vary between 10% to 300% of the weight of the adsorbent used. Specific amounts are specified in the examples that follow. The microcrystalline cellulose ingredient can be added rapidly with constant mixing at the highest workable speed, i.e., one that does not produce spillage or excessive dusting. Mixing times run 2-10 minutes or until uniform consistency is achieved. This step, as well as Step 1, is best performed in a humidity controlled room where the relative humidity is 40% or lower, preferably below 25%.

Step 3: Adding Silica

This final step provides for additional drying and producing enhanced flowability of the formula by adding special grades of silica ($SiO_2$). It can be done in the same mixer as steps 1 and 2: 0.25-2% by weight of the Step 2 mixture is added as silica, the Syloid 63 brand (W.R. Grace, Columbia, Md.) and the Pirosil brand (AIC, Inc., Framingham, Mass.) are preferred. The silica is added under constant mixing and mixing continues for 2-3 minutes or until uniformity is achieved. All steps 1-3 are to be conducted under Food Grade GMP procedures.

For enhanced drying, the silica can be heated in an oven at 450° F. for 8 hours and cooled prior to use. This is recommended when this product is added to formulations containing probiotic strains that have significant sensitivity to water activity.

Step 4: Packaging

The final formulation is packaged in airtight drums or bags and stored in a cool dry place until packaged or further processed. The shelf life, depending on the formula, will vary from 12-48 months. The percent active ingredient(s) in the final formulation will typically run from 5% to 40% depending on the formula. A sunflower lecithin formula using Hubersorb 600 as the adsorbent can contain up to 35% active ingredient (sunflower lecithin+vitamin E).

Final formulations from step 3 can be incorporated directly into probiotic formulations destined to be filled into capsules or sold as powders. The amount required to achieve a probiotic stimulation effect generally runs from 10 to 100 mg as active ingredient per probiotic dose, but more can be used. With a product that contains 30% active ingredient, a 10 mg active ingredient dose is achieved using about 33 mg of product for each probiotic dose in the probiotic formulation.

These results with various formulations made according to the above steps are provided in examples 4 to 10 below.

Example 2

Probiotic Cultures

The following probiotic cultures were obtained from Danisco in Madison, Wis. and were used in testing the prebiotic formulations:
*Lactobacillus acidophilus* NCFM (also called LA-1)
*Lactobacillus rhamnosus* Lr-32 (also called LR-44)
*Lactobacillus paracasei* Lpc-37 (also called F-19)
*Lactobacillus salavarius* Ls-33 (also called LS-30)
*Bifidobacterium lactis* B1-04 (also called BL-34)

Once a particular substitute ("active") ingredient for polysorbate 80 (i.e., sunflower lecithin, soy lecithin and/or oleic acid) is determined for a given probiotic strain by obtaining an equivalent or close to equivalent measure of growth and activity for that ingredient(s), it is formulated as in Example 1 to render it stable and non-reactive prior to ingestion and/or blending it into a commercial probiotic formulation. "Non-reactive" as used herein means that said rendered ingredient will not destabilize a finished probiotic formulation with respect to oxidation, redox potential, hygroscopicity, water activity, cell membrane integrity, and pH, or otherwise negatively affect probiotic activity.

Example 3

MRS Broth

MRS broth as used for testing of the formulation herein is made as follows, where the ingredients include:
Proteose Peptone #3: 10.0 g
Beef Extract: 10.0 g
Yeast Extract: 5.0 g
Glucose: 20.0 g
Polysorbate 80: 1.0 g (or substitute ingredient; or none for control)
Ammonium Citrate: 2.0 g
Sodium Acetate: 5.0 g
Magnesium sulfate: 0.1 g
Manganese sulfate: 0.05 g
Dipotassium phosphate: 2.0 g
Distilled Water: 1 liter The MRS broth was prepared in 1 liter screw cap Erlenmeyer flasks, as below in Example 4, for testing of various probiotic strains for growth and activity with just MRS broth (control), broth plus sunflower lecithin and/or oleic acid, and broth plus polysorbate 80.

Example 4

Testing Lecithins and/or Oleic Acid as Substitutes for Polysorbate 80 in the Growth of Probiotic Bacteria in MRS Broth MRS broth was prepared with polysorbate 80 (for controls) and without polysorbate 80 (for tests), and without polysorbate and with Lecithins and/or oleic acid instead (0.1% by weight of the broth), and filled into 1 liter screw cap flasks in equal amounts, which where were then autoclaved at 121° C. for 15 minutes. Each flask was tempered to 37° C. and aseptically inoculated with 0.14 gm of the individual probiotic strains (in Examples 5 to 10 below) to be tested. At specified time intervals, a 30 ml sample from each flask was aseptically transferred into a HACH 2100N Turbidimeter sample cell. The turbidity of each sample was read and the results were reported in NTU's.

The same 30 ml sample used for the turbidity reading was transferred into a 250 ml glass beaker, and the pH was recorded. The sample was titrated using 0.1N NaOH to an endpoint of pH 6.8, and the quantity of NaOH used was recorded. The % Lactic Acid was calculated using the following formula:

% Lactic Acid=((mls of 0.1N NaOH)×(0.1N)×(90 gm/mole)×(1 L/1000 ml))×100 mls of sample % Lactic Acid=(mls of 0.1N NaOH)×(0.9)

The results are presented in Exs. 5-10 below, and in the FIGS. 1A to 8B:

Example 5

Testing *L. acidophilus* NCFM (LA-1)

(Results reported at 12 hours and 23 hours like: 12/23 in Table I below)

TABLE I

| Lecithin/Oleic Acid in MRS | NTU (Turbidity) | Lactic Acid % | pH |
|---|---|---|---|
| None: included Polysorbate 80 in MRS | 1855/2038 | 1.09/1.27 | 4.2/4.1 |
| None, MRS only | 37/68 | 0.36/0.49 | 5.2/4.9 |
| 0.1% Sunflower Lecithin | 2015/2217 | 1.17/1.52 | 4.1/3.9 |
| 0.1% Soy Lecithin | 1962/2065 | 1.20/1.53 | 4.1/3.9 |
| 0.1% Oleic Acid | 1451/1789 | 1.03/1.21 | 4.3/4.1 |
| 0.1% Sunflower Lecithin + 0.1% OleicAcid | 2228/2877 | 1.19/1.57 | 4.1/4.0 |
| 0.05% Sunflower Lecithin | 895/1076 | 0.98/1.33 | 4.2/4.0 |
| 0.025% Sunflower Lecithin | 317/376 | 0.78/1.04 | 4.4/4.2 |
| 0.025% Oleic Acid | 498/603 | 0.70/0.77 | 4.5/4.4 |
| 0.025% Sunflower Lecithin + 0.025% Oleic Acid | 2273/2523 | 1.06/1.47 | 4.2/3.9 |
| 0.1% Sunflower Lecithin + 0.05% Oleic Acid | 2183/3193 | 1.16/1.53 | 4.1/3.9 |
|  |  | 0.98/1.33 |  |
| 0.05% Sunflower Lecithin + 0.05% Oleic Acid | 2330/2701 | 1.16/1.54 | 4.1/3.9 |

Example 5

Conclusions

Growth in MRS containing polysorbate 80 is the standard for comparison. Growth in MRS without either polysorbate 80 or one of the test additives is negligible, indicating the importance of such additives on probiotic growth. Both lecithins effectively replace polysorbate 80 at the 0.1% inclusion rates. The 0.05% inclusion rate for sunflower lecithin is at the lowest level of acceptable effectiveness; 0.025% is too low and does not yield acceptable stimulation. Oleic acid and sunflower lecithin are synergistic at the 0.025% inclusions levels, as the combined result is significantly greater than what was obtained by either additive alone at 0.025%. Oleic acid at 0.1% is somewhat effective as a polysorbate 80 replacement but not as effective as either sunflower or soy lecithin.

Example 6

Testing *Bifidobacterium lactic* Bl-04 (BL-34)

(Results reported at 12 hours and 23 hours like: 12/23 in Table II below)

TABLE II

| Lecithin/Oleic Acid in MRS | NTU (Turbidity) | Lactic Acid % | pH |
|---|---|---|---|
| None: included Polysorbate 80 in MRS | 922/1434 | 0.57/0.84 | 4.8/4.5 |
| None, MRS only | 20/32 | 0.15/0.23 | 5.4/5.3 |
| 0.1% Sunflower Lecithin | 1014/1532 | 0.6/0.92 | 4.8/4.5 |
| 0.1% Soy Lecithin | 868/1411 | 0.59/0.91 | 4.9/4.7 |
| 0.1% Sunflower Lecithin + 0.25% Oleic Acid | 1259/1979 | 0.66/0.99 | 4.8/4.5 |

Example 6

Conclusions

Growth in MRS containing polysorbate 80 is the standard for comparison. Growth in MRS without either polysorbate 80 or one of the test additives is negligible, indicating the importance of such additives for probiotic growth. Both lecithins (soy and sunflower) effectively replace polysorbate 80 at the 0.1% inclusion rates but sunflower lecithin gives the better result. Oleic acid and sunflower lecithin work at the 0.025% inclusion level for oleic acid and at 0.1% for sunflower lecithin, yielding a significant increase in turbidity (cell growth) and a slight increase in lactic acid production to sunflower lecithin alone.

Example 7

Testing *Lactobacillus paracasei* Lpc-37 (F-19)

(Results reported at 12 hours and 23 hours like: 12/23 in Table III below)

TABLE III

| Lecithin/Oleic Acid in MRS | NTU (Turbidity) | Lactic Acid % | pH |
|---|---|---|---|
| None: included Polysorbate 80 in MRS | 1664/2824 | 0.99/1.39 | 4.2/3.9 |
| None, MRS only | 21/43 | 0.26/0.36 | 5.4/5.1 |
| 0.1% Sunflower Lecithin | 1717/2813 | 0.91/1.34 | 4.2/3.9 |
| 0.1% Oleic Acid | 178/1789 | 0.33/1.01 | 5.1/4.1 |
| 0.1% Sunflower Lecithin + 0.1% OleicAcid | 335/2103 | 0.29/1.00 | 5.3/4.1 |

Example 7

Conclusions

Growth in MRS containing polysorbate 80 is the standard for comparison. Growth in MRS without either polysorbate 80 or one of the test additives is negligible, indicating the importance of such additives for probiotic growth. Sunflower lecithin effectively replaces polysorbate 80 at the 0.1% inclusion rate. Oleic acid at 0.1% shows an improvement over no polysorbate 80 but is not as effective a replacement for polysorbate 80 as sunflower lecithin. Oleic acid does not appear to be synergistic with sunflower lecithin at the concentrations studied.

Example 8

Testing *Lactobacillus rhamnosus*—Lr-32 (LR-44)

(Results reported at 12 hours and 23 hours like: 12/23 in Table IV below)

TABLE IV

| Lecithin/Oleic Acid in MRS | NTU (Turbidity) | Lactic Acid % | pH |
|---|---|---|---|
| None: included Polysorbate 80 in MRS | 2804/3776 | 1.12/1.67 | 4.0/3.7 |
| None, MRS only | 40/72 | 0.46/0.52 | 5.0/4.8 |
| 0.1% Sunflower Lecithin | 2572/3657 | 1.07/1.71 | 4.1/3.7 |
| 0.1% Oleic Acid | −30.9/2644 | 0.072/1.05 | 6.2/4.1 |
| 0.1% Sunflower Lecithin + 0.1% Oleic Acid | 57/3605 | 0.13/1.25 | 6.0/3.9 |

Example 8

Conclusions

Growth in MRS containing polysorbate 80 is the standard for comparison. Growth in MRS without either polysorbate 80 or one of the test additives is negligible, indicating the importance of such additives for probiotic growth. Sunflower lecithin effectively replaces polysorbate 80 at the 0.1% inclusion rate. Oleic acid at 0.1% shows an improvement over no polysorbate 80 on the 23-hour test but shows a significant lag phase at 12 hours; it is not as good a replacement for polysorbate 80 as sunflower lecithin. Oleic acid is not synergistic with sunflower lecithin at the concentrations studied.

Example 9

Testing *Lactobacillus salivarius*—Ls-33 (LS-30)

(Results reported at 12 hours and 23 hours like: 12/23 in Table V below)

TABLE V

| Lecithin/Oleic Acid in MRS | NTU (Turbidity) | Lactic Acid % | pH |
|---|---|---|---|
| None: included Polysorbate 80 in MRS | 3426/3931 | 1.42/1.68 | 3.8/3.7 |
| 0.1% Sunflower Lecithin | 3040/3283 | 1.36/1.60 | 3.9/3.8 |
| 0.1% Oleic Acid | 1440/3578 | 0.073/1.51 | 4.4/3.8 |

Example 9

Conclusions

Sunflower lecithin effectively replaces polysorbate 80 at the 0.1% inclusion rate. Oleic acid at 0.1% is not as good a replacement as a lag phase is apparent at 12 hours.

Example 10

Growth of the Commercial Probiotic THERALAC® in MRS Broth Containing Polysorbate 80, Compared to Oleic Acid and Lecithin MRS broth was prepared with (for controls) and without (for tests) polysorbate 80 and filled into 1 liter screw cap flasks at 500 ml each and autoclaved at 121° C. for 30 minutes. Various lecithin and/or oleic acid additives, or nothing (negative control), was added to the tests flasks prior to autoclaving. The flasks were then tempered to 37° C. in a water bath and inoculated at 0.1% with THERALAC® Lot #32310A, a commercial probiotic product (Master Supplements, Inc., Victoria, Minn.). Capsules of THERALAC® were opened and the contents mixed aseptically to serve as the inoculum source. At an inoculation rate of 0.1%, approximately 80 million CFU was added per ml of MRS media. THERALAC® contains (formulation strength) the following probiotic strains at the approximate CFU values listed per gram:
*Lactobacillus acidophilus* NCFM (LA-1): 30 billion CFU
*Bifidobacterium lactis* B1-04 (BL-34): 30 billion CFU
*Lactobacillus paracasei* Lpc-37 (F-19): 14 billion CFU
*Lactobacillus rhamnosus* Lr-32 (LR-44): 6 billion CFU
*Bifidobacterium lactis* Bi-07: 8 billion CFU Turbidity, pH and titrations (made with 0.1 N NaOH and reported as % lactic acid) were made at various times up to 23 hours. The results are presented below in Table VI for the 12 and 23-hour analyses.

TABLE VI (Results reported at 12 hours and 23 hours like: 12/23 in Table VI below)

| Lecithin/Oleic Acid in MRS | NTU (Turbidity) | Lactic Acid % | pH |
|---|---|---|---|
| None: included Polysorbate 80 in MRS | 3311/3694 | 1.42/1.84 | 3.9/3.7 |
| None, MRS only | 44/75 | 0.44/0.56 | 5.0/4.8 |
| 0.1% Sunflower Lecithin | 3343/3758 | 1.45/1.82 | 3.9/3.7 |
| 0.1% Soy Lecithin | 2939/3563 | 1.33/1.84 | 4.0/3.7 |
| 0.1% Oleic Acid | 2775/3529 | 1.18/1.72 | 4.1/3.8 |
| 0.1% Sunflower Lecithin + 0.1% OleicAcid | 2488/2917 | 1.20/1.72 | 4.0/3.8 |
| 0.1% Sunflower Lecithin + 0.025% Oleic Acid | 3447/3724 | 1.40/1.80 | 3.9/3.8 |
| 0.1% Soy Lecithin + 0.025% OleicAcid | 3190/3607 | 1.42/1.80 | 3.9/3.8 |

Example 10

(Theralac® Test) Conclusions

Growth in MRS containing polysorbate 80 is the standard for comparison. Growth in MRS without either polysorbate 80 or one of the test additives is negligible, indicating the importance of such additives for probiotic growth. Both lecithins effectively replace polysorbate 80 at the 0.1% inclusion rates but sunflower lecithin shows significantly more cell growth (turbidity) and lactic acid production at 12 hours, indicating a reduced lag phase. Oleic acid alone at 0.1% shows acceptable replacement value for polysorbate 80 but is not as effective as either of the lecithins. There appears to be a slight synergism between soy lecithin and oleic acid at the concentrations studied.

Example 11

Preparation of a Dry, Stable, Non-Reactive Prebiotic (DSNRP #1) for Use in Commercial Probiotic Formulations Step A: Add 250 grams of Hubersorb 600 to the bowl of a Kitchen Aid™ orbital mixer utilizing the wire wisp attachment.

Step B: In a separate container add 0.38 grams of natural vitamin E oil (Sigma Aldrich, St. Louis, Mo.) to 320 grams of sunflower lecithin (GIRALEC—Austrade, Inc., Palm Beach Gardens, Fla.) and 60 grams of extra-virgin olive oil. Mix thoroughly.

Step C: Start the agitation in the Kitchen Aid™ mixer at medium speed (about 40-50 RPM) and slowly pour in (add at approx. 100 ml/min.) the 380 grams of vitamin E treated sunflower lecithin plus olive oil. Mix for 2-3 minutes at medium-high speed (approximately 50-70 RPM) until the liquid is completely adsorbed.

Step C: While continuing to mix slowly add 560 grams of Microcel MC-132 microcrystalline cellulose (Blanver, Boca Raton, Fla.) and continue to mix for another 1-2 minutes.

Step D: Add 22 grams of Pirosil™ silica (AIC, Inc., Framingham Mass.) to the mixture and continue to mix for 2 additional minutes.

The final product is a free flowing white powder containing 26.4% sunflower lecithin by weight. DSNRP #1 for dry probiotic formulations (to be filled into capsules) would be 10% by weight of the formulation, where the probiotic dose rate is two 500 mg capsules per day. This provides 100 mg of DSNRP #1 containing 26 mg of active ingredient (sunflower lecithin). When these two capsules are taken with a 50 gram carbohydrate snack, the resulting concentration of lecithin will be 0.05%—an effective amount according to the results indicated herein.

Example 12

Preparation of a Dry, Stable, Non-Reactive Prebiotic (DSNRP #2) for Use in Commercial Probiotic Formulations Step A: Add 250 grams of Hubersorb 600 to the bowl of a Kitchen Aid™ orbital mixer utilizing the wire wisp attachment.

Step B: In a separate container add 0.38 grams of natural vitamin E oil (Sigma Aldrich, St. Louis, Mo.) to 320 grams of sunflower lecithin (GIRALEC—Austrade, Inc., Palm Beach Gardens, Fla.) and 60 grams of oleic acid (Sigma-Aldrich). Mix thoroughly.

Step C: Start the agitation in the Kitchen Aid™ mixer at medium speed (about 40-50 RPM) and slowly pour in (add at approx. 100 ml/min.) the 380 grams of vitamin E treated sunflower lecithin plus oleic acid. Mix for 2-3 minutes at medium-high speed (approximately 50-70 RPM) until the liquid is completely adsorbed.

Step C: While continuing to mix slowly add 560 grams of Microcel MC-132 microcrystalline cellulose (Blanver, Boca Raton, Fla.) and continue to mix for another 1-2 minutes.

Step D: Add 22 grams of Pirosil™ silica (AIC, Inc., Framingham, Mass.) to the mixture and continue to mix for 2 additional minutes.

The final product is a free flowing white powder containing 26.4% sunflower lecithin and 5% oleic acid by weight. DSNRP #2 in dry probiotic formulations (to be filled into capsules) would be preferably 10% by weight of the formulation, where the probiotic dose rate is two 500 mg capsules per day. This provides 100 mg of DSNRP #2 containing 26 mg of sunflower lecithin and 5 mg of oleic acid). When these two capsules are taken with a 50 gram carbohydrate snack, the resulting concentration of the combined active ingredients will be 0.062%—an effective amount according to the results indicated herein.

Example 13

Preparation of a Dry, Stable, Non-Reactive Prebiotic (DSNRP #3) for Use in Commercial Probiotic Formulations Step A: Add 780 grams of Perfectamyl D6 potato starch (National Starch-Avebe, Bridgewater, N.J.) to the bowl of a Kitchen Aid™ orbital mixer utilizing the wisp attachment for agitation.

Step B: In a separate container add 0.12 grams of natural vitamin E oil (Sigma-Aldrich, St. Louis, Mo.) to 100 grams of soy lecithin (ADM, Inc., Decatur, Ill.) and 20 grams of extra-virgin olive oil. Mix thoroughly.

Step C: Start the agitation in the Kitchen Aid™ mixer at about 40-50 RPM and slowly pour in (add at approx. 100 ml/min.) the 120 grams of liquid from step B. Mix for 3-4 minutes until completely adsorbed.

Step C: While continuing to mix slowly add 80 grams of Avicel PH112 brand (FMC Corp., Philadelphia, Pa.) microcrystalline cellulose and continue to mix for another 2-3 minutes.

Step D: Add 20 grams of Syloid 63 silica (W.R. Grace, Inc., Columbia, Md.) to the mixture and continue to mix for 3 additional minutes.

The final product is a free flowing white powder containing 10% active prebiotic ingredient (soy lecithin) by weight. DSNRP #3 for dry probiotic formulations (to be filled into capsules) would be 20% by weight of the formulation where the probiotic dose rate is two 500 mg capsules per day. This provides 200 mg of DSNRP #3 containing 20 mg of active ingredient (soy lecithin). When such a probiotic is taken with a 20 gram carbohydrate snack the resulting concentration of prebiotic will be 0.1%—an effective amount according to the results indicated herein.

Example 14

Preparation of a Dry, Stable, Non-Reactive Prebiotic (DSNRP #4) that can be Added to Commercial Probiotic Formulations Step A: Add 780 grams of food grade Kaolin clay (Vanclay, R.T. Vanderbilt Co., Norwalk, Conn.) in the bowl of a Kitchen Aid™ orbital mixer utilizing the pizza dough mixing impeller.

Step B: In a beaker add 0.12 grams of natural vitamin E oil (Sigma Aldrich, St. Louis, Mo.) to 100 grams of sunflower lecithin and 20 grams of olive oil. Mix thoroughly.

Step C: Start the agitation in the Kitchen Aid™ mixer at about 40-50 RPM and slowly pour in (add at approx. 100 ml/min.) the 120 grams of vitamin E treated sunflower lecithin plus olive oil. Mix for 3-4 minutes.

Step C: While continuing to mix slowly add 80 grams of Microcel MC-132 microcrystalline cellulose and continue to mix for another 2-3 minutes.

Step D: Add 20 grams of Pirosil silica to the mixture and continue to mix 3 additional minutes.

The final product is a free flowing beige-colored powder containing 10% active prebiotic ingredient (sunflower lecithin) by weight. DSNRP #4 for dry probiotic formulations (to be filled into capsules) would be 20% by weight of the formulation, where the probiotic dose rate is two 500 mg capsules per day. This provides 200 mg of DSNRP #4 containing 20 mg of active ingredient (sunflower lecithin). When such a probiotic is taken with a 20 gram carbohydrate snack the resulting concentration of prebiotic will be 0.1%—an effective amount according to the results indicated herein.

Example 15

Direct Dietary Supplement Use of DSNRP Prebiotic Formulations

The DSNRP formulations from examples 11-14 can be filled into hard capsules such as gelatin or HPMC capsules, or any other capsule types suitable for use with dietary supplements, in such sizes as 50 mg to 1,000 mg, and utilized for direct consumption as a dietary supplement independent of any probiotic product, or can be taken with a probiotic product, or the probiotic product can be included in the formulation. As noted above, all such formulations preferably include an enteric coating; for example, the one described in U.S. Pat. Nos. 7,229,818 and 7,122,370 (incorporated by reference). Magnesium stearate at 2-3% by weight of the DSNRP formulas should be included to serve as an encapsulating lubricant. Tablets and caplets can also be produced from the DSNRP formulations as an option to capsules. Final encapsulated or tableted DSNRP products should be packaged in hermetically sealed plastic or glass bottles with moisture absorbent packets and the finished products should be stored under cool conditions. The separate formulations can be administered before or after administering probiotics, under any of a number of dosing schedules.

The foregoing examples, other terms and expressions, are given for the purpose of illustrating various embodiments of the invention and, along with the methods described herein, are representative of preferred embodiments, are exemplary, and are not intended as limitations on the scope of the invention. Changes therein and other uses which are encompassed within the spirit of the invention as defined by the claims, will occur to those skilled in the art. The invention is defined only in the claims which follow and includes all equivalents of the claims.

What is claimed is:

1. A prebiotic formulation for stimulating the growth and lactic acid producing activity of *Lactobacillus* or *Bifidobacterium* species of probiotic bacteria comprising:
   a dry powdered form formulation of sunflower lecithin, or combinations of sunflower lecithin and oleic acid; and
   wherein the formulation is substantially free of polysorbate 80.

2. The formulation of claim 1 further including Vitamin E.

3. The method formulation of claim 1 wherein the weight ratio of the sunflower lecithin lecithin's to oleic acid is from 60:40 to 95:5.

4. The formulation of claim 1, in a caplet or capsule.

5. The formulation of claim 2, wherein Vitamin E is the D, L or a mixture of the D and L isomers.

6. The formulation of claim 2, wherein the Vitamin E is 0.05 to 2% by weight of the formulation.

7. The formulation of claim 3, wherein the ratio of sunflower lecithin to oleic acid is 90:10.

8. The formulation of claim 4, wherein the caplet or capsule has an enteric coating.

9. A dry powdered form prebiotic formulation for stimulating the growth and lactic acid producing activity of *Lactobacillus* or *Bifidobacterium* species of probiotic bacteria comprising:
   a dry powdered form formulation of sunflower lecithin or oleic acid, or combinations of sunflower lecithin and oleic acid, adsorbed to an adsorbent which is one or more of calcium silicate, silicon dioxide, silica, clays and food starches, and mixed with microcellulose and silica; and
   wherein the formulation is substantially free of polysorbate 80.

10. The formulation of claim 9, wherein the sunflower lecithin or oleic acid, or the combinations of sunflower lecithin and oleic acid, are non-aqueous.

11. The formulation of claim 9, wherein the sunflower lecithin or oleic acid, or the combinations of sunflower lecithin and oleic acid, are in a capsule, caplet, tablet or other carrier together with *Lactobacillus* and/or *Bifidobacterium* species.

12. The formulation of claim 9, wherein the food starches are corn starch or potato starch.

13. The formulation of claim 9, wherein the clays are food grade.

14. The formulation of claim 9, wherein the microcrystalline cellulose carrier is between 10% to 300% of the weight of the adsorbent.

15. The formulation of claim 9, wherein the combined weight of the lecithin and oleic acid is 5 to 40% of the weight of the formulation.

16. The formulation of claim 9, wherein the silica is 0.25% to 2.0% by weight of the formulation.

17. The formulation of claim 9 wherein the weight ratio of the sunflower lecithin to oleic acid is from 60:40 to 95:5.

18. The formulation of claim 11, wherein the strains of *Lactobacillus* include *Lactobacillus acidophilus* NCFM, *Lactobacillus rhamnosus* Lr-32, *Lactobacillus paracasei* Lpc-37, 25 and *Lactobacillus salavarius* Ls-33.

19. The formulation of claim 11, wherein the *Bifidobacterium* is *Bifidobacterium lactis* B1-04 (BL-34).

20. The formulation of claim 11, wherein the tablet, caplet, capsule or carrier has an enteric coating.

21. The formulation of claim 13, wherein the clays are kaolin or sodium bentonite.

22. The formulation of claim 17, wherein the ratio of sunflower lecithin to oleic acid is 90:10.

* * * * *